US006221877B1

(12) United States Patent
Aronov et al.

(10) Patent No.: US 6,221,877 B1
(45) Date of Patent: Apr. 24, 2001

(54) SUBSTITUTED 4-PHTHALIMIDOCARBOXANILIDES AS INHIBITORS OF PURINE SALVAGE PHOSPHORIBOSYLTRANSFERASES

(75) Inventors: Alex M. Aronov; Narsimha R. Munagala; Paul R. Ortiz de Montellano, all of San Francisco; Irwin D. Kuntz, Greenbrae; Ching C. Wang, San Francisco, all of CA (US)

(73) Assignee: Regents of the University of California, Oakland, CA (US)

( * ) Notice: Subject to any disclaimer, the term of this patent is extended or adjusted under 35 U.S.C. 154(b) by 0 days.

(21) Appl. No.: 09/547,531

(22) Filed: Apr. 12, 2000

(51) Int. Cl.$^7$ .................. A61K 31/473; A61K 31/4035; C07D 219/10; C07D 209/48; A61N 33/02; A61P 33/02

(52) U.S. Cl. .................... 514/297; 514/414; 514/417; 546/105; 548/462; 548/463; 548/474; 548/480; 548/479

(58) Field of Search ..................... 514/417, 297, 514/414; 546/105; 548/480, 462, 463, 474, 479

(56) References Cited

U.S. PATENT DOCUMENTS 3,356,672 * 12/1967 Schefczik .............................. 260/152
5,514,813 * 5/1996 Brunelle ............................... 548/462

OTHER PUBLICATIONS

Aldritt, Susan M., et al., "Purification and Characterization of Guanine Phosphoribosyltransferase From Giardia Lamblia", *The Journal of Biological Chemistry*, vol. 261:8528–8533 (1986).
Aronov, Alex M., et al., Phthalimide Resin Reagent for Efficient Mitsunobu Amino–Dehydroxylation, *Tetrahedron Letters*, vol. 39:4947–4950 (1998).
Aronov, Alex M., et al., Rational Design of Selective Submicromolar Inhibitors of Tritrichomonas foetus Hypoxanthine–Guanine–Xanthine Phosphoribosyltransferase, *Biochemistry*, vol. 39(16) Apr. 25, 2000.
Beck, Joanne T., et al., "The Hypoxanthine–Guanine–Xanthine Phosphoribosyltransferase From Tritrichomonas Foetus Has Unique Properties", *Molecular and Biochemical Parasitology*, vol. 60:187–194 (1993).
Chin, Marian S., et al., Isolation, Sequencing and Expression of the Gene Encoding Hypoxanthine–Guanine–Xanthine Phosphoribosyltransferase of Tritrichomonas Foetus, *Molecular and Biochemical Parasitology*, vol. 63:221–230 (1994).
Eads, et al., "The Crystal Structure of Human Hypoxanthine–Guanine Phosphoribosyltransferase with Bound GMP", *Cell* vol. 78:325–334 (1994).
Gutteridge, W.E., "Designer Drugs: Pipe–Dreams or Realities?", *Parasitology*, vol.114:S145–S151 (1997).

Hague, Tasir S., et al., "Potent, Low–Molecular–Weight Non–Peptide Inhibitors of Malarial Aspartyl Protease Plasmepsin II", *Journal of Medicinal Chemistry*, vol. 42:1428–1440 (1999).
Hunter, W.N., A Structure–Based Approach to Drug Discovery; Crystallography and Implications for the Development of Antiparasite Drugs, *Parasitology*, vol.114:S17–S29 (1997).
Kanaaneh, Jamil, et al., Differntial Inhibitory Effects of GMP–2',3'–Dialdehyde on Human and Schistosomal Hypoxanthine–Guanine Phosphoribosyltransferases, *Eur. J. Biochem.*, vol. 223:595–601 (1994).
Lapinski, Christopher A., et al., "Experimental and Computational Approaches to Estimate Solubility and Permeability in Drug Discovery and Development Settings", *Advanced Drug Delivery Reviews* vol. 23:3–25 (1997).
Schumacher, Maria A., et al., "Crystal Structures of Toxoplasma Gondii HGXPRTase Reveal the Catalytic Role of a Long Flexible Loop", *Nature Structural Biology*, vol. 3:881–887 (1996).
Shi, Wuxian, et al., The 2.0 Å Structure of Human Hypoxanthine–Guanine Phosphoribosyltransferase in Complex wth a Transition–State Analog Inhibitor, *Nature Structural Biology*, vol. 6:588–593 (1999).
Shi, Wuxian, et al., The 2.0 Å Structure of Malarial Purine Phosphoribosyltransferase in Complex with a Transition–State Analogue Inhibitor, *Biochemistry*, vol. 38:9872–9880 (1999).
Sommer, Jürg M., et al., "Cloning, Expression and Characterization of an Unusual Guanine Phosphoribosyltransferase from Giardia Lamblia", *Molecular and Biochemical Parasitology*, vol. 78:185–193 (1996).
Somoza, John R., et al., "Rational Design of Novel Antimicrobials: Blocking Purine Salvage in a Parasitic Protozoan", *Biochemistry*, vol. 37(16):5344–5348 (1998).
Somoza, John R., et al., "Crystal Structure of Hypoxanthine–Guanine–Xanthine Phosphoribosyltransferase from the Protozoan Parasite Tritrichomonas Foetus", *Biochemistry*, vol. 35:7032–7040 (1996).
Wang, C.C., "Current Problems in Anti–Parasite Chemotherapy", *Trends in Biochemical Sciences*, vol. 7:354–356 (1982).
Wang, C.C., "Parasite Enzymes as Potential Targets for Antiparasitic Chemotherapy", *Journal of Medicinal Chemistry*, vol. 27:1–9 (1984).
Wang, C.C., et al., "Purine Salvage by Tritrichomonas Foetus", *Molecular and Biochemical Parasitology*, vol. 8:325–337 (1983).
Wang, C.C. "Validating Targets for Antiparasite Chemotherapy", *Parasitology*, vol. 114:S31–S44 (1997).
Yuan, Ling, et al., Steady–State Kinetics of the Schistosomal Hypoxanthine–Guanine Phosphoribosyltransferase, *Biochemistry*, vol.31:806–810 (1992).

* cited by examiner

Primary Examiner—Floyd D. Higel
Assistant Examiner—Sonya N. Wright
(74) *Attorney, Agent, or Firm*—Cooley Godward LLP

(57) ABSTRACT

The use of certain heterocyclic derivatives for treating parasitic protozoa infections in mammals, in particular bovine trichomoniasis and giardiasis, is disclosed.

22 Claims, No Drawings

SUBSTITUTED 4-PHTHALIMIDOCARBOXANILIDES AS INHIBITORS OF PURINE SALVAGE PHOSPHORIBOSYLTRANSFERASES

This invention was made with Government Support under Grant Nos. AI-19319, GM31497 and GM56531, awarded by the National Institutes of Health. The Government has certain rights to this invention.

BACKGROUND OF THE INVENTION

FIELD OF THE INVENTION

This invention pertains to novel heterocyclic derivatives that are useful for treating parasitic protozoa infections in mammals, in particular bovine trichomoniasis and giardiasis.

RELATED DISCLOSURES

Parasitic protozoa infections in mammals are widespread and difficult to prevent or remedy effectively. For example, *Tritrichomonas foetus* is an anaerobic protozoan parasite that causes bovine trichomoniasis in cattle; it is prevalent in cattle herds throughout much of the world, and causes a substantial loss in beef production. *Gardia lamblia* is an example of a water-borne zoonotic protozoan parasite; it is also found worldwide, and infection leads to severe diarrhea and growth retardation in humans.

It has been observed that parasitic protozoa lack a de novo purine nucleotide synthetic pathway (Wang, *Trends Biochem. Sci.* 7:354–356 (1982)). Instead, they utilize purine salvage pathways to convert the host organism's purine bases and nucleosides to the corresponding nucleotides (Wang, *J. Med. Chem.* 27:1–9 (1984)). Purine phosphoribosyltransferases (PRTs) are a class of enzymes that catalyze the reaction of a purine with α-D-S-phosphoribosyl-1-pyrophosphate (PRPP) to produce nucleotide monophosphates via nucleophilic displacement of pyrophosphate. Inhibiting PRTs could represent an efficient approach to antiparasite chemotherapy if these enzymes provide the primary means of purine salvage for the parasite (Wang, *Parasitology* 114:S31–S44 (1997)).

*Tritrichomonas foetus*, an anaerobic flagellated protozoan that causes urogenital trichomoniasis in cattle, relies primarily on a single enzyme, hypoxanthine-guanine-xanthine phosphoribosyltransferase (HGXPRT) to replenish its purine nucleotide pool (Wang, et al., *Mol. Biochem. Parasitol.* 8:325–337 (1983)). Similarly, *G. lamblia* relies upon the guanine phosphoribosyltransferase enzyme (GPRT) for supplying its guanine nucleotide pool.

It is apparent that inhibition of the purine salvage pathways of the parasitic protozoa would be an effective way to block the ability of the parasites to survive in the host. However, it is important that any compounds capable of such an inhibiting effect should not interfere with the host hypoxanthine-guanine phosphoribosyltransferase (HGPRT). For example, in humans defects in HGPRT are known to be responsible for gouty arthritis and a number of central nervous system disorders.

To assist in the identification of compounds that selectively inhibit purine salvage pathways, both enzymes (HGXPRT from *T. foetus* and GPRT from *G. lamblia*) were purified to homogeneity and partially characterized (Beck, et al., *Mol. Biochem. Parasitol.* 60:187–194 (1993); Aldritt, et al., *J. Biol. Chem.* 261:8528–8533 (1986)). The genes encoding the two enzymes were cloned, sequenced and expressed in transformed *Escherichia coli* to produce large quantities of recombinant enzyme proteins in their native state (Chin, et al., *Mol. Biochem. Parasitol.* 63:221–230 (1994); Sommer, et al., *Mol. Biochem. Parasitol.* 78:185–193 (1996)). The purified recombinant *T. foetus* HGXPRT was crystallized and the crystal structure was determined by X-ray crystallography (Somoza, et al., *Biochemistry* 35:7032–7040 (1996)). The X-ray structure of this enzyme is a useful tool in the search for novel scaffolds that could be used to design new selective inhibitors of HGXPRT. Computer modeling of the active site in the enzyme molecule was initiated in the laboratory of Professor Irwin Kuntz to identify chemical compounds that conform to the dimensions of (and complement the chemistry of) the pocket and thus inhibit the enzyme function.

A group of heterocyclic compounds have been identified that conform to the dimensions of the pocket and complement its chemistry, and inhibit the purine salvage pathways of the parasites without affecting the mammalian HGPRT, and are described in Wang, et al, U.S. Ser. No. 09/118,451 and Somoza, et al., *Biochemistry* 37(16): 5344–5348 (1998). However, in spite of these advances in the field, there continues to remain a need for HGXPRT inhibitors having better potency and improved affinity and selectivity.

Rapid growth in the field of parasite structural biology, spurred by recent advances in parasite biology and biochemistry, is becoming increasingly important in the process of drug discovery for parasitic infections (Hunter, *Parasitology* 114:S17–S29(1997)). A combination of rational target selection with molecular modeling tools, aided by new combinatorial chemistry technologies, has become a method of choice for designing potent and selective ligands for a number of targets in parasites (Gutteridge, *Parasitology* 114:S145–S151 (1997); Haque, et al., *J. Med. Chem.* 42:1428–1440 (1999)). This technology, and continued efforts to use the X-ray structure of the *T. foetus* HGXPRT-guanosine 5'-monophosphate complex, have now provided a novel group of heterocyclic compounds that bind tightly to the purine pocket of HGXPRT and are selective submicromolar inhibitors of *T. foetus* HGXPRT.

SUMMARY OF THE INVENTION

The present invention relates to compounds of Formula I:

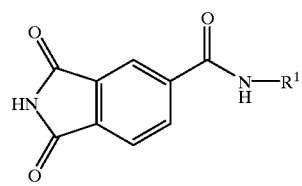

wherein: $R^1$ is selected from the group consisting of:

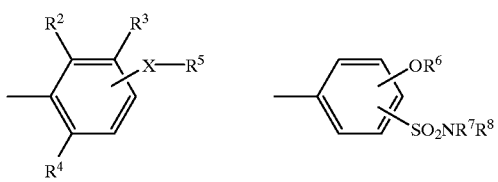

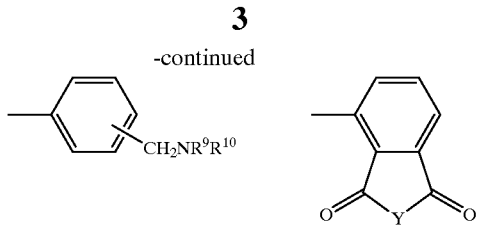
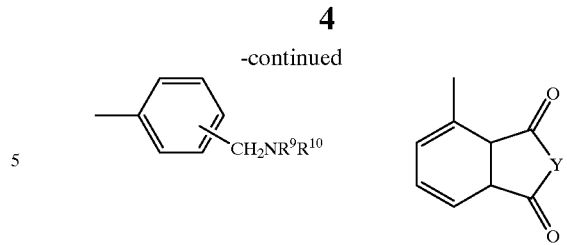

and a fused three-membered aryl or heteroaryl group; $R^2$, $R^3$ and $R^4$ are independently selected from the group consisting of H, lower alkyl and halo; X is selected from the group consisting of —$CH_2$—O— and —O—$CH_2$—; $R^5$ is aryl; $R^6$, $R^7$ and $R^8$ are independently selected from the group consisting of H and lower alkyl; $R^9$ is lower alkyl and $R^{10}$ is a cyclic aliphatic ring, or $R^9$ and $R^{10}$ can be taken together to form a cyclic aliphatic ring; Y is selected from the group consisting of NH and O; and the pharmaceutically acceptable salts thereof.

One aspect of the invention relates to a method of treating parasitic protozoa infections in mammals, which method comprises administering to a mammal in need of such treatment a therapeutically effective amount of a compound of Formula I.

Yet another aspect of the invention pertains to a pharmaceutical composition containing a therapeutically effective amount of a compound of Formula I in a pharmaceutically acceptable carrier.

DETAILED DESCRIPTION OF THE INVENTION

The invention relates to a family of substituted 4-phthalimidocarboxanilide compounds. These compounds inhibit growth of *T. foetus* parasite culture by selectively interfering with parasite purine salvage as inhibitors of the parasite's HGXPRT competitive with the purine substrate. Accordingly, this family of compounds is useful for treating disease states that are caused by parasitic protozoa. In particular, these compounds are useful for treating disease states in mammals by inhibiting hypoxanthine-guanine-xanthine phosphoribosyltransferase or guanine phosphoribosyltransferase in the purine salvage pathways of the parasitic protozoa responsible for the disease state.

The compounds of the invention have the Formula I:

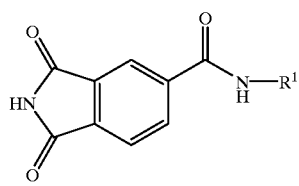

I wherein: $R^1$ is selected from the group consisting of:

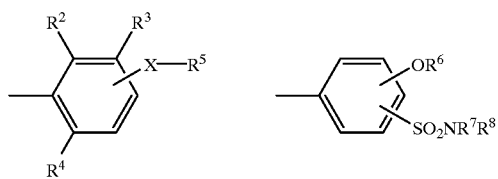

and a fused three-membered aryl or heteroaryl group; $R^2$, $R^3$ and $R^4$ are independently selected from the group consisting of H, lower alkyl and halo; X is selected from the group consisting of —$CH_2$—O— and —O—$CH_2$—; $R^5$ is aryl; $R^6$, $R^7$ and $R^8$ are independently selected from the group consisting of H and lower alkyl; and $R^9$ is lower alkyl and $R^{10}$ is a cyclic aliphatic ring, or $R^9$ and $R^{10}$ can be taken together to form a cyclic aliphatic ring; Y is selected from the group consisting of NH and O; and the pharmaceutically acceptable salts thereof.

The compounds of Formula I can be easily produced from inexpensive starting materials, an important feature of any potential anti-parasitic agent. The invention also contemplates varying the anilide portion of these inhibitors in a solid phase format in response to emerging resistance, which is another feature that could potentially enable rapid access to newly improved inhibitors with increased efficacy against the resistant strains. The compounds of the invention are sufficiently small (MW<500) and lipophilic (clogP values vary in the 3.85–4.70 range for the most active compounds as calculated using the clogP program (*Daylight,* version 4.61, Daylight Chemical Information Systems, Inc., Santa Fe, N. Mex. (1997)). In addition, they contain 2 hydrogen bond donors and 4 hydrogen bond acceptors, thus satisfying Lipinski rules (Lipinski, et al., *Adv. Drug Deliv. Rev.* 23:3–25 (1997)) for compounds best suited for passing through biological membranes.

As is described in detail herein, the compounds of the invention are micromolar phthalimide-based inhibitors for phosphoribosyltransferases with differing specificities, including human HGPRT and *Giardia lamblia* GPRT.

Definitions

As used herein:

The term "alkyl" means a branched or unbranched saturated monovalent hydrocarbon radical containing 1 to 8 carbon atoms, such as methyl, ethyl, propyl, tert-butyl, n-hexyl, n-octyl and the like.

The term "lower alkyl" means a branched or unbranched saturated monovalent hydrocarbon radical containing 1 to 6 carbon atoms, such as methyl, ethyl, propyl, isopropyl, tert-butyl, butyl, n-hexyl and the like, unless otherwise indicated.

The term "cyclic aliphatic ring" means a saturated hydrocarbon ring containing 5 to 7 carbon atoms, such as cyclopentane, cyclohexane, and the like. The term "cyclic aliphatic ring" is also intended to include saturated rings containing one or more heteroatoms (e.g. cyclic ethers, piperidyl, and the like).

The term "lower alkoxy" means the group —O-(lower alkyl) wherein lower alkyl is as herein defined.

The term "halo" means the halogen radical fluoro, chloro, bromo, or iodo.

The term "aryl" refers to a monovalent unsaturated aromatic carbocyclic radical having a single ring (e.g., phenyl) or two rings (e.g., naphthyl or biphenyl), which can unsubstituted or mono-, di- or tri-substituted, independently, with —OH, —COOH, —CH$_2$—SO$_2$-phenyl, lower alkyl, lower alkoxy, halo, nitro, amino, alkylamino, dialkylamino, trifluoromethyl and/or cyano.

The term "heteroaryl" refers to a monovalent aromatic carbocyclic radical having 1–3 heteroatoms within a single ring, (e.g., such as pyridyl, imidazolyl, thiazolyl, pyrimidine, oxazolyl, and the like), or within two rings (e.g., indolyl, quinolinyl, benzofuranyl, and the like) which can optionally be mono-, di- or tri-substituted, independently, with OH, COOH, lower alkyl, lower alkoxy, halo, nitro, amino, alkylamino, dialkylamino, trifluoromethyl and/or cyano.

The term "fused three-membered aryl or heteroaryl group" means three aryl or heteroaryl rings, as defined above, that are fused together (e.g. acridinyl, anthryl, and the like).

The term "heteroatom" refers to oxygen, sulfur and nitrogen, unless otherwise specified.

The term "q.s" is used herein to mean adding a quantity sufficient to achieve a stated function., for example to bring a solution to a desired volume (q.s. to 100 ml) or to a desired pH (q.s. to pH 4).

As used herein, the terms "inert organic solvent" or "inert solvent" mean a solvent inert under the conditions of the reaction being described in conjunction therewith {including, for example, benzene, toluene, acetonitrile, tetrahydrofuran ("THF"), dimethylformamide ("DMF"), chloroform ("CHCl$_3$"), methylene chloride (or dichloromethane or "CH$_2$Cl$_2$"), diethyl ether, ethyl acetate, acetone, methylethyl ketone, methanol, ethanol, propanol, isopropanol, tertbutanol, dioxane, pyridine, and the like}. Unless specified to the contrary, the solvents used in the reactions of the present invention are inert solvents.

"Optional" or "optionally" means that the subsequently described event or circumstance may or may not occur, and that the description includes instances where said event or circumstance occurs and instances in which it does not. For example, "optionally substituted aryl" means that the aryl may or may not be substituted and that the description includes both unsubstituted aryl and substituted aryl.

It should be understood that Formula I, as drawn, is intended to represent the racemic form of compounds of Formula I as well as the individual enantiomers and nonracemic mixtures thereof. Accordingly, the scope of the invention as described and claimed encompasses the racemic forms of the compounds of Formula I as well as the individual enantiomers and non-racemic mixtures thereof.

The term "pharmaceutically acceptable salt" means those salts which retain the biological effectiveness and properties of the compounds of Formula I, and which are not biologically or otherwise undesirable. Such salts may be prepared from inorganic and organic bases. Salts derived from inorganic bases include, but are not limited to, the sodium, potassium, lithium, ammonium, calcium, and magnesium salts. Salts derived from organic bases include, but are not limited to, salts of primary, secondary and tertiary amines, substituted amines including naturally-occurring substituted amines, and cyclic amines, including isopropylamine, trimethylamine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, and N-ethylpiperidine. It should also be understood that other carboxylic acid derivatives would be useful in the practice of this invention, for example carboxylic acid amides, including carboxamides, lower alkyl carboxamides, di(lower alkyl) carboxamides, and the like.

The term "treatment" as used herein covers any treatment of a disease in a mammal, particularly a human, and includes: (i) preventing the disease from occurring in a subject which may be predisposed to the disease but has not yet been diagnosed as having it; (ii) inhibiting the disease, i.e. arresting its development; or (iii) relieving the disease, i.e. causing regression of the disease.

The term "disease state which is alleviated by treatment with an inhibitor of the purine salvage pathways of parasitic protozoa" as used herein is intended to cover all disease states which are generally acknowledged in the art to be usefully treated with inhibitors of the purine salvage pathways of parasitic protozoa in general, and those disease states which have been found to be usefully treated by the specific compounds of our invention, the compounds of Formula I.

The tern "therapeutically effective amount" refers to that amount which is sufficient to effect treatment, as defined above, when administered to a mammal in need of such treatment. The therapeutically effective amount will vary depending on the subject and disease state being treated, the severity of the affliction and the manner of administration, and may be determined routinely by one of ordinary skill in the art.

One example of a compound of Formula I is illustrated below in order to demonstrate the numbering system used in the nomenclature for describing such compounds:

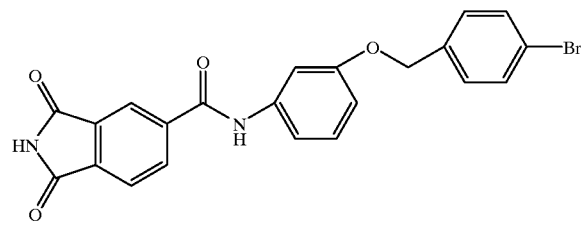

This is a compound of Formula I where R$^1$ is:

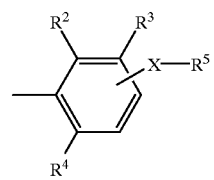

R$^2$, R$^3$ and R$^4$ are H; X is —O—CH$_2$—; and R$^5$ is aryl mono-substituted with a halo group. This compound is named (4'-phthalimido)carboxamido-3-(4-bromobenzyloxy)-benzene and is referred to herein as compound Ia(5).

The compounds of Formula I can also be described as having Formula Ia, Formula Ib, Formula Ic, Formula Id or Formula Ie, each one corresponding to a particular R$^1$ substituent. Compounds of particular interest include those listed in Tables I–V below, where the R groups and X and Y substituents correspond to those defined for Formula I. It is to be understood that the compounds shown are merely representative and not exhaustive. Others will be apparent to those of skill in the art, given this disclosure.

Compounds of Formula Ia have the formula:

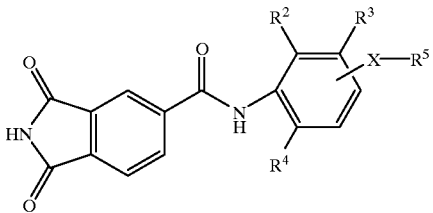

Ia where: $R^2$, $R^3$, $R^4$, X and $R^5$ are as defined above for Formula I; and the pharmaceutically acceptable salts thereof. The following table illustrates some exemplary and/or preferred compounds and substituents of the invention.

TABLE I

Formula Ia Compounds

| Compound # | $R^2$ | $R^3$ | $R^4$ | X* | $R^5$ |
|---|---|---|---|---|---|
| Ia(1) | H | H | H | —O—CH$_2$— | phenyl |
| Ia(2) | H | —CH$_3$ | H | —CH$_2$—O— | phenyl |
| Ia(3) | Cl | H | H | —O—CH$_2$— | phenyl |
| Ia(4) | H | H | —CH$_3$ | —O—CH$_2$— | phenyl |
| Ia(5) | H | H | H | —O—CH$_2$— | 4-bromophenyl |
| Ia(6) | H | H | H | —O—CH$_2$— | 4-methylphenyl |
| Ia(7) | H | H | H | —O—CH$_2$— | 3,5-dimethoxy phenyl |
| Ia(8) | H | H | H | —O—CH$_2$— | naphthyl |
| Ia(9) | H | H | H | —O—CH$_2$— | 3-iodophenyl |
| Ia(10) | H | H | H | —O—CH$_2$— | 2-iodophenyl |
| Ia(11) | H | H | H | —O—CH$_2$— | (1-phenyl sulfonyl-methyl) phenyl (at 1-position) |
| Ia(12) | H | H | H | —O—CH$_2$— | 3,4-dichloro phenyl |
| Ia(13) | H | H | H | —O—CH$_2$— | 2,6-dichloro phenyl |
| Ia(14) | H | H | H | —O—CH$_2$— | 2,5-dichloro phenyl |
| Ia(15) | H | H | —CH$_3$ | —O—CH$_2$— | 4-bromophenyl |
| Ia(16) | H | H | —CH$_3$ | —O—CH$_2$— | 3,4-dichloro phenyl |

*X is at the 3-position

Compounds of Formula Ib have the formula:

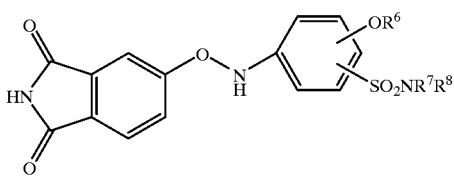

Ib where $R^6$, $R^7$ and $R^8$ are as defined above for Formula I; and the pharmaceutically acceptable salts thereof. The following table illustrates some exemplary and/or preferred compounds and substituents of the invention.

TABLE II

Formula Ib Compounds

| Compound # | $R^6$ | $R^7$ | $R^8$ |
|---|---|---|---|
| Ib(1) | —CH$_3$— | —CH$_2$CH$_3$ | —CH$_2$CH$_3$ |

Compounds of Formula Ic have the formula:

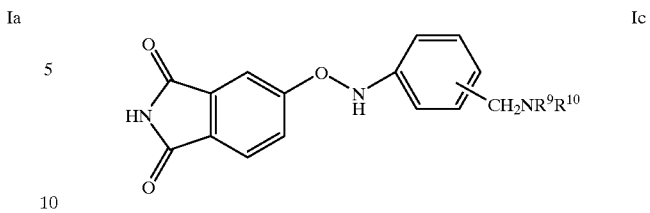

Ic where $R^9$ and $R^{10}$ are as defined above for Formula I; and the pharmaceutically acceptable salts thereof. The following table illustrates some exemplary and/or preferred compounds and substituents of the invention.

TABLE III

Formula Ic Compounds

| Compound # | $R^9$ | $R^{10}$ |
|---|---|---|
| Ic(1) | —CH$_3$ | cyclohexyl |
| Ic(2) | —CH$_3$ | cyclic ether |

Compounds of Formula Id have the formula:

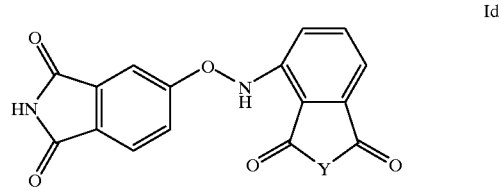

Id where Y is defined above for Formula I; and the pharmaceutically acceptable salts thereof. The following table illustrates some exemplary and/or preferred compounds and substituents of the invention.

TABLE IV

Formula Id Compounds

| Compound # | Y |
|---|---|
| Id(1) | —NH— |
| Id(2) | —O— |

Compounds of Formula Ie have the formula where $R^1$ is a fused three-membered aryl or heteroaryl group; and the pharmaceutically acceptable salts thereof. The following table illustrates some exemplary and/or preferred compounds and substituents of the invention.

TABLE V

Formula Ie Compounds

| Compound # | $R^1$ |
|---|---|
| Ie(1) | acridinyl |
| Ie(2) | anthryl |

Methods of Preparation

The starting materials are either commercially available, for example from Sigma Chemicals, Aldrich, Maybridge Chemicals, and so forth or alternatively may be prepared by means well known in the art. The desired aniline compounds are commercially available, or are synthesized as described herein or by methods that are well known in the art.

Compounds of Formula Ia, Ib and Ic are prepared as shown in Scheme I. Trimellitic anhydride, an exceptionally inexpensive starting material due to its broad application in polymer synthesis, is converted to 4-carboxyphthalimide at 280° C. using ammonium carbonate, and the scaffold is attached to the trityl chloride-functionalized resin. The resin serves the dual purpose of providing support for solid phase synthesis and protecting the imide nitrogen. Coupling to the aniline library is carried out under standard conditions in DIPEA/DMA. Both bromo-tris-pyrrolidino-phosphonium hexafluorophosphate (PyBrOP) and benzotriazole-1-yl-oxy-tris-pyrrolidino-phosphonium hexafluorophosphate can be used, with PyBrOP being preferred. To increase the coupling yields, the resin is typically incubated at 37° C. for an extended period of time (5–7 days) to provide yields varying from 5% to 95%.

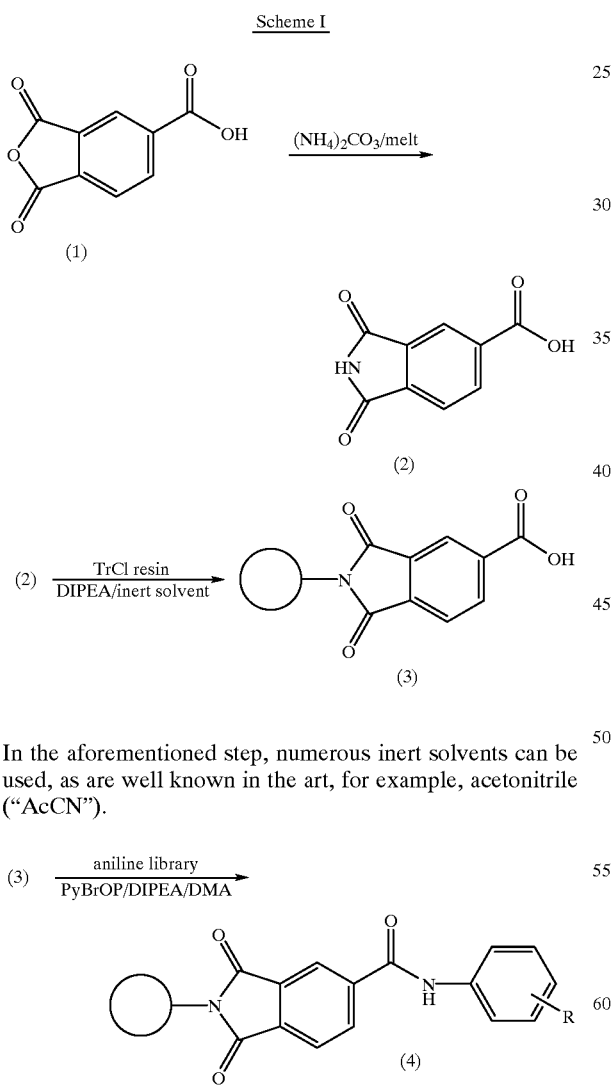

In the aforementioned step, numerous inert solvents can be used, as are well known in the art, for example, acetonitrile ("AcCN").

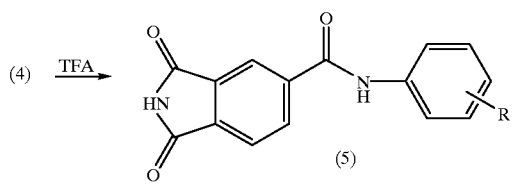

Aniline compounds for the synthesis of compounds of Formula Ia, where X is —CH$_2$—O— are prepared as follows:

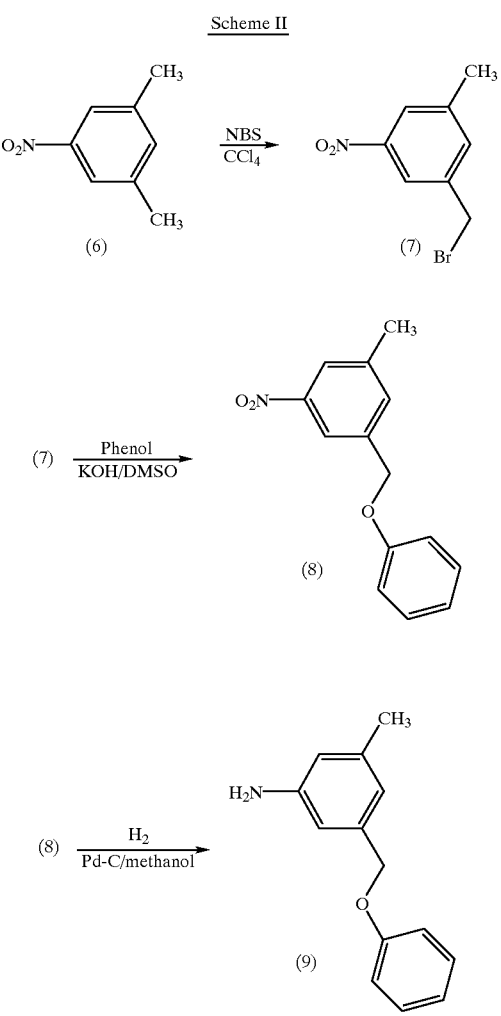

Aniline compounds for the synthesis of compounds of Formula Ia, where X is —O—CH$_2$— are prepared as follows:

Scheme III

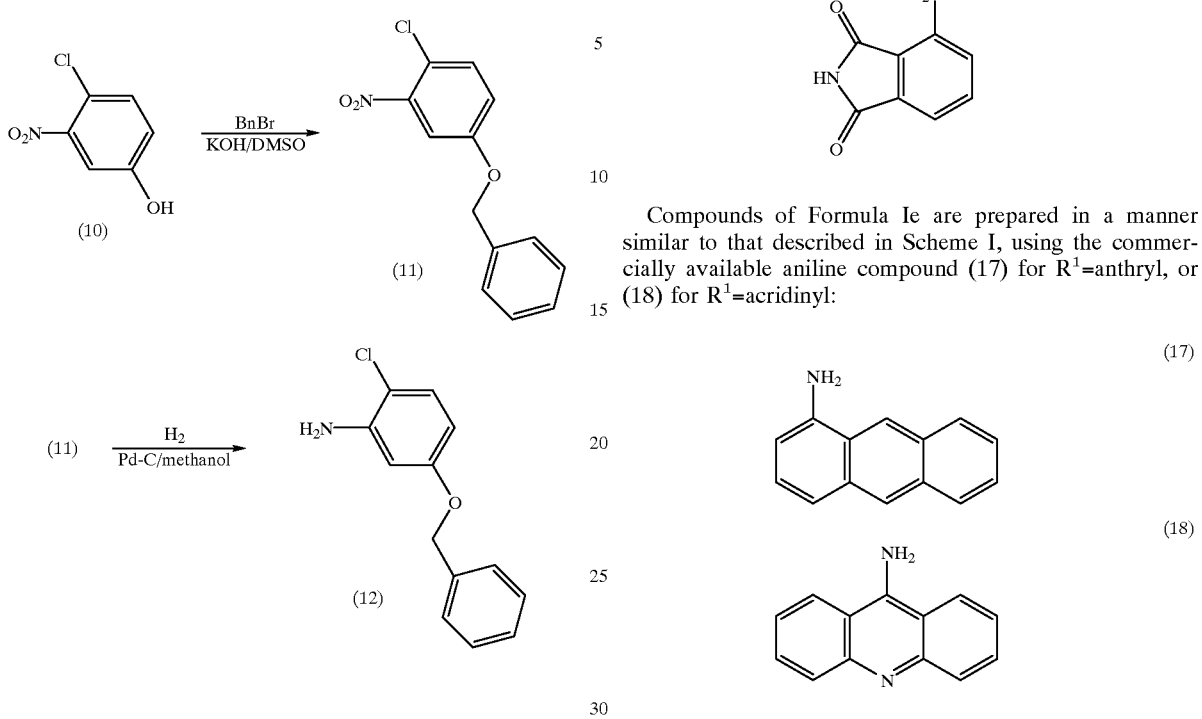

Compounds of Formula Ib are prepared in a manner similar to that described in Scheme I, using the commercially available compound (13) as the aniline:

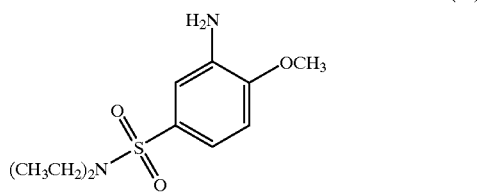
(13)

Compounds of Formula Ic are prepared in a manner similar to that described in Scheme I, using the commercially available compound (14) as the aniline:

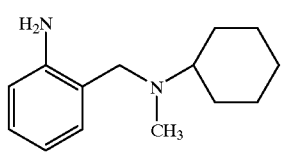
(14)

Compounds of Formula Id are prepared in a manner similar to that described in Scheme I, using the commercially available compound (15) as the aniline:

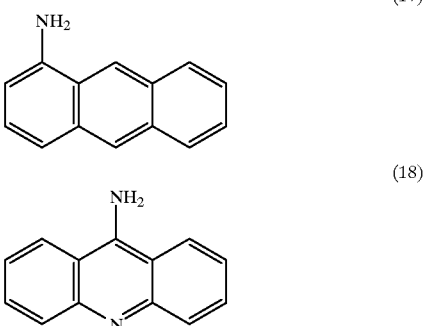

Compounds of Formula Ie are prepared in a manner similar to that described in Scheme I, using the commercially available aniline compound (17) for $R^1$=anthryl, or (18) for $R^1$=acridinyl:

General Utility

The compounds of Formula I and the pharmaceutically acceptable salts thereof have been found to possess valuable pharmacological properties, and have been shown to be useful as selective inhibitors of the purine salvage pathways of parasitic protozoa. Accordingly these compounds and pharmaceutically acceptable compositions containing them are useful for treating parasitic protozoa infections, and in particular are useful for the treatment of trichomoniasis and giardiasis.

A virtual library of substituted 4-phthalimidocarboxanilides was first constructed using methods of structure-based drug design, and was implemented synthetically on solid support. Subsequent evaluation of these compounds lead to the discovery of a secondary lead (identified herein as compound Ia(1)) for a second round of combinatorial chemistry, producing a number of low micromolar inhibitors of HGXPRT. One of these compounds (identified herein as compound Ia(5)), was further characterized as a competitive inhibitor of T. foetus HGXPRT with respect to guanine with $K_1$=0.49 μM and a 30-fold selectivity over the human HGPRT. Compound Ia(5) inhibited the growth of cultured T. foetus cells in a concentration-dependent manner with $ED_{50}$=2.8 μM, and this inhibitory effect could be reversed by addition of exogenous hypoxanthine. These studies underscore the efficiency of combining structure-based drug design with combinatorial chemistry to produce effective species-specific enzyme inhibitors of medicinal importance, further details of which are described in Aronov, et al., "Rational Design of Selective Submicromolar Inhibitors of *Tritrichomonas foetus* Hypoxanthine-Guanine-Xanthine Phosphoribosyltransferase", *Biochemistry* 39(16): 4569–4962 (2000).

Accordingly, one aspect of the invention relates to a method of treating parasitic protozoa infections in mammals, which method comprises administering to a mammal in need of such treatment a therapeutically effective amount of a compound of Formula I. More particularly, the invention pertains to a method of treating in mammals a disease state that is alleviated by treatment with an inhibitor of hypoxanthine-guanine-xanthine phosphoribosyltransferase or guanine phosphoribosyltransferase in the purine salvage pathways of parasitic protozoa, which method comprises administering to a mammal in need of such treatment a therapeutically effective amount of a compound of Formula I.

Testing

The potential of the compounds for utility against parasitic protozoa infections, in particular *Tritrichomonas foetus* and *Giardia lamblia,* is determined by the method described in Example 1, of Wang, et al., *Mol. Biochem. Parasitol.* 8:325–337 (1983).

General Administration

In applying the compounds of this invention to treatment of the above conditions, administration of the active compounds and salts described herein can be via any of the accepted modes of administration, including oral, parenteral and otherwise systemic route of administration. Any pharmaceutically acceptable mode of administration can be used, including solid, semi-solid or liquid dosage forms, such as, for example, tablets, suppositories, pills, capsules, powders, liquids, suspensions, or the like, preferably in unit dosage forms suitable for single administration of precise dosages, or in sustained or controlled release dosage forms for the prolonged administration of the compound at a predetermined rate. The compositions will typically include a conventional pharmaceutical carrier or excipient and an active compound of Formula I or the pharmaceutically acceptable salts thereof and, in addition, may include other medicinal agents, pharmaceutical agents, carriers, adjuvants, etc.

Accordingly, one aspect of the invention pertains to a pharmaceutical composition containing a therapeutically effective amount of a compound of Formula I in a pharmaceutically acceptable carrier. More specifically, the invention relates to a composition for the treatment of parasitic protozoa infections in mammals by inhibiting hypoxanthine-guanine-xanthine phosphoribosyltransferase or guanine phosphoribosyltransferase in the purine salvage pathways of said parasitic protozoa, which composition comprises a compound of Formula I in a pharmaceutically acceptable carrier.

The amount of active compound administered will of course, be dependent on the subject being treated, the severity of the affliction, the manner of administration and the judgment of the prescribing physician. However, an effective dosage is in the range of 0.1–50 mg/kg/day, preferably 1–20 mg/kg/day. For an average 70 kg human, this would amount to 7 to 3500 mg per day, or preferably 70 to 1400 mg/day.

For solid compositions, conventional non-toxic solid carriers include, for example, pharmaceutical grades of mannitol, lactose, starch, magnesium stearate, sodium saccharin, talcum, cellulose, sodium croscarmellose, glucose, sucrose, magnesium carbonate, and the like may be used. The active compound as defined above may be formulated as suppositories using, for example, polyalkylene glycols, for example, propylene glycol, as the carrier. Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see *Remington's Pharmaceutical Sciences,* Mack Publishing Company, Easton, Pa., 16th Edition, 1980. The composition or formulation to be administered will, in any event, contain a quantity of the active compound(s) in an amount effective to alleviate the symptoms of the subject being treated.

Dosage forms or compositions containing active ingredient (compounds of Formula I or its salts) in the range of 0.025 to 95 wt % with the balance made up from non-toxic carrier may be prepared.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, sodium croscarmellose, glucose, sucrose, magnesium, carbonate, and the like. Such compositions take the form of solutions, suspensions, tablets, capsules, powders, sustained release formulations and the like. Such compositions may contain 0.1–95 wt % active ingredient, preferably 0.5–80 wt %.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795, which is hereby incorporated by reference.

The percentage of active compound contained in such parental compositions is highly dependent on the specific nature thereof, as well as the activity of the compound and the needs of the subject. However, percentages of active ingredient of 0.01 wt % to 10 wt % in solution are employable, and will be higher if the composition is a solid which will be subsequently diluted to the above percentages. Preferably the composition will comprise 0.02–8 wt % of the active agent in solution.

For systemic administration via suppository, traditional binders and carriers include, e.g. polyalkylene glycols or triglycerides. Such suppositories may be formed from mixtures containing active ingredient in the range of 0.05–10 wt %; preferably 0.1–2 wt %.

In applying the compounds of the invention to treatment of diseases or disorders of the eye which are associated with an abnormally high intraocular pressure, administration may be achieved by any pharmaceutically acceptable mode of administration which provides adequate local concentrations to provide the desired response. These include direct administration to the eye via drops and controlled release inserts or implants, as well as systemic administration as previously described.

Drops and solutions applied directly to the eye are typically sterilized aqueous solutions containing 0.001 wt % to 10 wt %, most preferably 0.005 wt % to 1 wt % of the active ingredient, along with suitable buffer, stabilizer, and preservative. The total concentration of solutes should be such that, if possible, the resulting solution is isotonic with the lacrimal fluid (though this is not absolutely necessary) and has an equivalent pH in the range of pH 6–8. Typical sterilants are phenyl mercuric acetate, thimerosal, chlorobutanol, and benzalkonium chloride. Typical buffer systems and salts are based on, for example, citrate, borate or phosphate; suitable stabilizers include glycerin and polysorbate 80. The aqueous solutions are formulated simply by dissolving the solutes in a suitable quantity of water, adjusting the pH to about 6.8–8.0, making a final volume adjustment with additional water, and sterilizing the preparation using methods known to those in the art.

The dosage level of the resulting composition will, of course, depend on the concentration of the drops, the condition of the subject and the individual magnitude of responses to treatment. However, a typical ocular composition could be administered at the rate of about 2–10 drops per day per eye of a 0.1 wt % solution of active ingredient.

The compositions of the present invention may also be formulated for administration in any convenient way by analogy with other topical compositions adapted for use in mammals. These compositions may be presented for use in any conventional manner with the aid of any of a wide variety of pharmaceutical carriers or vehicles. For such topical administration, a pharmaceutically acceptable non-toxic formulation can take the form of semisolid, liquid, or solid, such as, for example, gels, creams, lotions, solutions, suspensions, ointments, powders, or the like. As an example, the active components may be formulated into a gel using ethanol, propylene glycol, propylene carbonate, polyethylene glycols, diisopropyl adipate, glycerol, water, etc., with appropriate gelling agents, such as Carbomers, Klucels, etc. If desired, the formulation may also contain minor amounts of non-toxic auxiliary substances such as preservatives, antioxidants, pH buffering agents, surface active agents, and the like. Actual methods of preparing such dosage forms are known, or will be apparent, to those skilled in the art; for example, see *Remington's Pharmaceutical Sciences*, Mack Publishing Company, Easton, Pa., 16th Edition, 1980. The preparations described in the examples illustrate the invention but are not intended to limit its scope.

EXAMPLES

| ABBREVIATIONS | |
|---|---|
| ACD | Available Chemicals Database |
| CGI | Common Gateway Interface |
| BnBr | benzyl bromide |
| DIPEA | diisopropylethylamine |
| DMA | dimethylacetamide |
| DMF | dimethylformamide |
| DMSO | dimethyl sulfoxide |

-continued

| ABBREVIATIONS | |
|---|---|
| GMP | guanosine 5'-monophosphate |
| HGPRT | hypoxanthine-guanine phosphoribosyltransferase |
| HGXPRT | hypoxanthine-guanine-xanthine phosphoribosyltransferase |
| HPLC | high performance liquid chromatography |
| NBS | N-bromosuccinimide |
| PyBrOP | bromo-tris-pyrrolidino-phosphonium hexafluorophosphate |
| SMILES | Simplified Molecular Input Line Entry System |
| TFA | trifluoroacetic acid |
| TLC | thin layer chromatography |

MATERIALS AND METHODS

A. Materials

Commercially available materials were purchased from sources such as Aldrich. Trityl chloride resin and PyBrOP were purchased from Novabiochem (San Diego, Calif.). All anhydrous solvents were obtained from Aldrich (Milwaukee, Wis.). TLC was carried out with precoated silica gel $F_{254}$ plates from Analtech (Newark, Del.), and spots were detected under UV light (254 nm). Ninhydrin staining was used for detection of amines. Flash chromatography was carried out with silica gel (230–400 mesh, Merck). The UV source used for photochemical brominations was Spectroline ENF-280C (17 W) from Spectronics Corp. (Westbury, N.Y.). NMR spectra were taken on Varian (Palo Alto, Calif.) Inova 400 and Inova 600 spectrometers. Key target compounds were purified by reverse phase HPLC on a $C_{18}$ column from Alltech (Deerfield, Ill.) with a $CH_3OH/H_2O$ elution gradient. Purity was confirmed by using a $C_4$ column from Vydac (Hesperia, Calif.). The HPLC interface consisted of Rainin HPXL solvent delivery modules and a Rainin Dynamax UV-1 UV-VIS spectrophotometric detector with UV detection at 254 nm. HPLC solvents were of the highest grade commercially available and were used as received.

B. Structure Analysis

The crystal structure of *T. foetus* HGXPRT (1 hgx) was determined by Somoza, et al., *Biochemistry* 35:7032–7040 (1996), and the crystal structure of the human HGPRT (1 hmp) was determined by Eads, et al., *Cell* 78:325–334 (1994). The software packages Sybyl (*Sybyl*, version 6.5, Tripos Associates, St. Louis, Mo. (1999)) and Insight II (*Insight II*, version 98.0, Molecular Simulations, Inc., San Diego, Calif. (1998)) were used for display and analysis of the structures.

C. Database Mining

UC_Select (Skillman, A. G., and Kuntz, I. D., unpublished results) in combination with the Daylight version of ACD was used to identify original reagent sets, as well as for the elimination of reagents that had unattractive chemical or pharmaceutical properties. UC_React (Skillman, A. G., and Kuntz, I. D., unpublished results) interfaced with Sybyl's CONCORD module was used to build the virtual library for docking. Similarity and superstructure searches of the ACD were performed with Daylight's Merlin system (*Daylight*, version 4.61, Daylight Chemical Information Systems, Inc., Santa Fe, N. Mex. (1997)), using a Tanimoto similarity metric and Daylight's hashed connectivity fingerprints.

D. Docking

DOCK4.01 (Ewing, et al., (1997) *J. Comput. Chem.* 18, 1175–1189) was used to screen the virtual phthalimide library in order to limit the size of the primary library. A typical docking process involves: (a) creating a negative image of the active site using sphere sets, (b) matching existing sphere sets to molecules in the library, (c) scoring and ranking compounds based on goodness of fit, and (d) reviewing the conformations of the best-scoring compounds. The approach taken in this study differed from the general method in the following aspects: (a) xanthine was mapped onto the guanine moiety of GMP, and the 6-oxo/1-NH of xanthine were matched to the O=C—NH—C=O portion of phthalimide; in order to facilitate correct matching, spheres at positions C1 and C3 in the benzene ring of phthalimide were removed from the sphere set, and the sphere for carbon C2 was specified for chemical matching; (b) in every case preorientation of the library with the sphere set (orientation search without scoring) followed by rigid docking of the preoriented library (orientation search with scoring for rigid molecules) and subsequent flexible scoring (scoring of a variety of conformations for selected orientations) gave the best results. In modeling substituents in the aniline ring of compound Ia(1), the DOCK-derived conformation for compound Ia(1) was used as a starting point for flexible docking.

Example 1

Structure-Based Drug Design and Combinatorial Chemistry

A. Choice of Scaffold and Chemistry

The first step in inhibitor design involved scaffold modification. A good choice of a scaffold would lack any residual reactive functionalities, would be easily amenable to combinatorial modification, preferably in a solid phase format, and would not be associated with any known toxicities. Phthalimide appeared to fit all of these criteria. Nearly isosteric with phthalic anhydride, it presented an imide functionality suitable for attachment to the resin. A number of substituted phthalimides have been looked at as potential medicinal candidates, and had not been associated with any specific kind of toxicity. In addition, the imide portion of the molecule looks very similar to the C6-N1-C2 of xanthine, one of the natural substrates of HGXPRT. Since human HGPRT does not act on xanthine, the phthalimide scaffold could potentially have built-in selectivity for the parasite enzyme.

To test this hypothesis, (4'-phthalimido)carboxamido-3,4-dichlorobenzene was prepared. This compound is the phthalimide analog of 5-[N-(3,4-dichlorophenyl) carbamoyl]-1,3-isobenzofurandione, both of which are described in Wang, et al., U.S. Ser. No. 09/118,451. (4'-phthalimido)carboxamido-3,4-dichlorobenzene was shown to be equally active on HGXPRT as 5-[N-(3,4-dichlorophenyl)carbamoyl]-1,3-isobenzofurandione.

Evaluation of the introduction of a flexible linker (between one and three methylene units) that would serve to attach the amide to the aromatic ring, lead to the preparation of a library of phthalimidocarboxanilides to identify selective HGXPRT inhibitors.

B. Primary Library Generation

The first step was to create a virtual library of anilines available for attachment to the phthalimide scaffold. Initial datable mining was transformed using the UC_Select program (Eads, et al., Cell 78:325–334 (1994)). It is a web-based CGI program which provides an interface to search the Daylight version of the ACD database for compounds with desired structural features. The program also provides for efficient Lipinski role-based (Lipinski, et al., Adv. Drug Deliv. Rev. 23:3–25 (1997)) elimination of compounds possessing undesirable structural features, i.e. filtering out the non-druglike compounds by placing limits on molecular weight, lipophilicity, number of charges, and hydrogen bond donors and acceptors. Optional extra SMILES arguments allow for additional customizable filtration protocols. This search provided a list of 873 anilines. Following removal of unreactive aminopurines and arninopyrimidines, and subsequent visual inspection to remove anilines with 3 or more electron-withdrawing substituents, as well as di-ortho substituted compounds, the library was reduced to a final size of 599 molecules.

The next step was to prepare the virtual phthalimidocarboxanilide library. UC_React uses recursive SMARTS (Daylight, version 4.61, Daylight Chemical Information Systems, Inc., Santa Fe, N. Mex. (1997)) to conduct user-defined chemistry in silico. It deletes atoms not present in the final product, and then joins the resulting fragments together. This program was applied to the aniline collection to produce a library of phthalimide derivatives with varying anilide chains. The resulting virtual library was used in docking experiments, and a final library was eventually selected for synthesis.

For an antiparasite drug to have any practical relevance, it should be relatively easy to prepare from inexpensive starting materials. A straightforward chemical scheme was thus implemented to access a variety of substituted phthalimidocarboxanilides (Scheme I). Compounds were synthesized and tested, with compounds Id(1) and Ia(1) having good $IC_{50}$ values, as can be seen in Table 1 of Example 12.

C. Compound Ia(1) As a Starting Point for Design of the Secondary Library

In light of the activity data, the models were reevaluated in search of a reasonable secondary lead compound. The phthalimide compound Ia(1) appeared best suited for that role in that it was the second most potent member of the library, the conformation originally proposed by DOCK was similar to the minimized conformation of an unbound ligand, and the benzyl ether linkage made the compound easily amenable to further combinatorial exploration.

In studying the model of the HGXPRT:compound Ia(1) complex, it was observed that the phthalimide portion of the inhibitor appeared slightly displaced from the position of the purine base. The anilide moiety is positioned between Thr 107 and Thr 110, implicated in binding the 5-phosphate of GMP. The specificity for anilides at that position can be explained by the shallowness of the loop formed by residues 107–111, and the hydrophobic interactions of the aromatic ring of the anilide with the side chains of Leu 109 and Met 111. According to the model, the second aromatic ring attached to the anilide via the oxymethylene linker should also contribute the hydrophobic interactions with Leu 109. The nine residue loop from Tyr 74 to Asn 82 acts as a flap and covers the catalytic pocket to shield the oxocarbonium transition state from nucleophilic attack by bulk solvent (See Schumacher, et al., Nature Struct. Biol. 3:881–887 (1996); Shi, et al., Nature Struct. Biol. 6:588–593 (1999); and Shi, et al., Biochemistry 38:9872–9880 (1999)). This flexible loop was disordered in the X-ray structure of T. foetus HGXPRT, and thus complicated the analysis of the contribution of the loop to inhibitor binding. The carbonyl of Ser 73 was a mere 3.3 Å away from the face of the aromatic ring, underscoring the importance of that part of the protein in forming the binding pocket for compound Ia(1). The binding model for the phthalimide inhibitor, compound Ia(1) closely resembled the model of T. foetus HGXPRT-bound phthalic anhydride-based inhibitor containing a 3-nitroanilide moiety which was described in Somoza, et al., Biochemistry 37:5344–5348 (1998). The two models were obtained independently using different docking protocols.

D. Effect of Substitutions in the Anilide Ring of Compound Ia(1).

Initial exploration focused on the binding pocket for the anilide moiety of compound Ia(1). Perturbations in this portion of compound Ia(1) were modeled by redocking the modified inhibitors into the HGXPRT binding site. Small hydrophobic substitutions were slightly preferred at positions 2, 5, and 6 of the anilide ring, while no additional group could be accommodated at position 4. The directionality of the oxymethylene linker did not affect the docking score for analogs of compound Ia(1), which allowed for greater synthetic flexibility in the design of target molecules.

Compounds Ia(2), Ia(3) and Ia(4) were prepared using the solid phase format as described herein. The corresponding anilines were prepared using standard chemistry (Schemes II and III) via reduction of the respective 3-substituted nitrobenzenes. It was found that the introduction of the methyl substituent at position 2 led to a significant increase in enzyme inhibition over the unmodified inhibitor. Since the substitution at that position would be expected to directly affect the conformation of the oxymethylene linker, a possible explanation for the observed increase in affinity of Ia(4) for HGXPRT could involve repositioning of the benzyloxy moiety within the enzyme's active site.

E. Synthesis of a Secondary Library

The second stage of focus involved optimization of the 3-benzyloxy substituent. Keeping the core intact, the effect of various substituents in the benzyl fragment on activity was evaluated. The synthetic scheme involved introducing diversity at the first aniline-building step by alkylation of 3-nitrophenol with a variety of substituted benzyl bromides. Reduction of the nitroaromatics yielded a library of anilines that could be coupled to the resin to produce additional analogs of compound Ia(1).

Since the substituted benzyl derivatives of compound Ia(1) would most likely interact with the flexible loop portion of HGXPRT, no preliminary requirements were placed on the starting benzyl bromide library. The available compounds were first searched for benzyl bromide superstructures. Compounds having undesirable functionalities (UC_Select) were eliminated to provide a final group of 48 substituted benzyl bromides. By clustering these compounds with a complete-linkage hierarchical clustering program, ten clusters and eleven singletons were obtained. Of these, twelve compounds were chosen by visual inspection as the representatives of various clusters so that they describe much of the geometric variability for mono- and di-substituted benzyl bromides. Compounds in this secondary library produced an improvement over the lead compound Ia(1), with the most active inhibitors being compounds Ia(5) and Ia(6), bearing small hydrophobic substituents in the p-position of the benzyl fragment, 4'-bromo and 4'-methyl, respectively. As shown in Tables 1 and 2, these inhibitors represented a 10-fold increase in affinity for T. foetus HGXPRT compared to compound Ia(1). Compound Ia(12), having a 3'-chloro in addition to a 4-chloro substituent, also faired reasonably well, its $IC_{50}$ being nearly 5-fold lower than that of compound Ia(1).

Having found the best individual combinations for both the anilide and the benzyl moieties comprising inhibitor Ia(1), the 2-methyl modification (Ia(4)) was combined with substitutions at the 4'-position (Ia(5) and Ia(6)). The resulting inhibitors (Ia(15) and Ia(16)) had less potency, but are still viable drug candidates. This finding indirectly supports the initial hypothesis that the 2-methyl substituent in compound Ia(4) induces a conformational change (most likely for the 3-benzyloxy group) which constitutes a departure from the conformations assumed by inhibitors Ia(1), Ia(5) and Ia(6).

Example 2

Synthesis of 4-Carboxyphthalimide (2)

The title compound (2) was obtained, using commercially available trimellitic anhydride (1) as a starting material, by melting trimellitic anhydride with ammonium carbonate at 280° C. as described in Aronov, et al., *Tetrahedron Lett.* 39:4947–4950 (1998). $^1$H NMR (DMSO-$d_6$) δ7.93 (d, 1, H6), 8.07 (s, 1, H3), 8.14 (d, 1, H5).

Example 3

Synthesis of N-Trityl-4-Carboxyphthalimide Resin (3)

To trityl chloride resin (5 g; 10.25 retool; 200–400 mesh: 1% divinylbenzene-crosslinked polystyrene) presoaked in 80 mL dry acetonitrile for 30 min., 5 g (26 mmol) 4-carboxyphthalimide (2) from Example 2 and 6 mL (34 mmol) DIPEA were added, and the suspension was refluxed for 72 h. Following filtration, the polymer was washed with 300 mL DMF and then 300 mL $CH_2Cl_2$. The loading was determined by weight difference, and confirmed to be 0.5 mmol/g resin by TFA-induced cleavage of 4-carboxyphthalimide from the resin.

Example 4

Aniline Coupling/Product Cleavage Procedure

To 100 mg of resin (0.06 mmol 4-carboxyphthalimide) (3) from Example 3, presoaked in 2 mL DMA for 30 min., were added 0.56 g (20 eq) PyBrOP, 0.52 mL (50 eq) DIPEA, and 1.2 mmol (20 eq) of the desired aniline. The suspension was shaken for 5 days at 37° C., followed by filtration to remove excess reagents. The resin was washed with 5 mL DMF, 5 mL ethyl acetate, 5 mL methanol, and 10 mL $CH_2Cl_2$, and was then air dried to yield the resin-bound product (4). To facilitate cleavage of the target compounds (5), the resin was suspended in 2 mL TFA for 4 h. The resin was removed by filtration, the resulting filtrate was dried in vacuo, and the product was loaded onto a short plug of silica gel. Quick elution with ethyl acetate allowed for removal of colored impurities undesirable in a spectrophotometric assay.

Example 5

Synthesis of 3-Methyl-5-Nitrobenzyl Bromide (7)

To a solution of 0.8 g (5.3 mmol) of commercially available m-nitroxylene (6) in 10 mL $CCl_4$, 1.23 g (6.9 mmol, 1.3 eq) NBS was added, and the mixture was irradiated with a UV source at reflux for 4 h. The resulting mixture was dried in vacuo, suspended in hexane, and filtered. The filtrate was dried to afford a 10:1:3 mixture of monobromide:starting material:dibromide. The title material (7) was purified in 65% yield by silica gel chromatography using a 0–5% ethyl acetate/hexane gradient. $^1$H NMR $(CDCl_2)$ δ2.46 (s, 3, $CH_3$), 4.48 (s, 2, $CH_2$), 7.52 (s, 1, H2), 7.97 (s, 1, H4), 8.05 (s, 1, H6).

Example 6

Synthesis of (3-Methyl-5-Phenoxymethyl) Nitrobenzene (8)

3-Methyl-5-nitrobenzyl bromide (0.8 g, 3.5 mmol) (7) from Example 5 was dissolved in 10 mL DMSO, followed by the addition of 0.46 g (4.9 mmol, 1.4 eq) phenol and 300 mg (5.3 mmol) potassium hydroxide. The solution was stirred for 2 h, until essentially all the potassium hydroxide dissolved. The reactants were diluted into 30 mL of ethyl acetate, and washed twice with an equal volume of water. The organic layer was dried with sodium sulfate, and the solvent was removed in vacuo. Silica gel purification (in hexane, followed by 0–5% ethyl acetate/hexane gradient) afforded the title product (0.81 g, 95%) (8). $^1$H NMR (CDCl$_3$) δ2.49 (s, 3, CH$_3$), 5.11 (s, 2, CH$_2$), 6.95–7.03 (m, 3, phenolic H$_p$ and 2 H$_m$), 7.24–7.34 (m, 2, phenolic 2 H$_o$), 7.58 (s, 1, H2), 7.99 (s, 1, H6), 8.11 (s, 1, H4).

Example 7

Synthesis of (3-Methyl-5-Phenoxymethyl)Aniline (9)

To a solution of 0.81 g (3.3 mmol) (3-Methyl-5-phenoxymethyl)nitrobenzene (8) from Example 6 in 10 mL methanol, 30 mg Pd/C catalyst was added, and the mixture was shaken under H$_2$ for 2 h (35 psi). The resulting solution was filtered through Celite and the solvent was removed in vacuo. The title product (9) was purified on silica gel (hexane/ethyl acetate) to homogeneity (0.64 g, 90% yield). $^1$H NMR (CDCl$_3$) δ2.25 (s, 3, CH3), 4.92 (s, 2, CH2), 6.4–6.7 (3s, 3, H2, H4, H6), 6.95–6.97 (m, 3, phenolic H$_p$ and 2 H$_m$), 7.20–7.28 (m, 2, phenolic 2 H$_o$).

Example 8

Synthesis of (3-Benzyloxy-6-Chloro)Nitrobenzene (11)

Commercially available 4-chloro-3-nitrophenol (10) (1 g, 5.7 mmol) was dissolved in 10 mL DMSO, followed by the addition of 0.97 g (5.7 mmol, 1.0 eq) BnBr and 400 mg (7.1 mmol) potassium hydroxide. The solution was stirred for 2 h, until essentially all the potassium hydroxide dissolved. The reactants were diluted into 30 mL of ethyl acetate, and washed twice with an equal volume of water. The organic layer was dried with sodium sulfate, and the solvent was removed in vacuo. Silica gel purification (in hexane, followed by 0–5% ethyl acetate/hexane gradient) afforded the title compound (1.4 g, 93%) (11). $^1$H NMR (CDCl$_3$) δ5.10 (s, 2, CH$_2$), 7.11 (dd, 1, H4), 7.38–7.43 (m, 6, phenyl and H5), 7.46 (d, 1, H2).

The title compound (11) can then be used in the method described in Example 7 to produce (3-benzyloxy-6-chloro) aniline (12).

Example 9

Synthesis of (4'-Phthalimido)Carboxamido-3-Methyl-5-Phenoxymethylbenzene (Ia(2))

The title compound (Ia(2)) was synthesized following the method of Example 4 and using the aniline (9) from Example 7. $^1$H NMR (DMSO-d$_6$) δ2.30 Cs, 3, CH$_3$), 5.04 Cs, 2, CH$_2$), 6.90–7.05 (m, 4, phenyl H$_p$+2H$_o$, H4), 7.24–7.30 (m, 2, 2H$_m$), 7.56, 7.65 (2s, 2, H2, H6), 7.93 (d, 1, H6'), 8.32 (d, 1, H5'), 8.33 (s, 1, H3').

Example 10

Synthesis of (4'-Phthalimido)Carboxamido-3-Benzyloxy-6-Chlorobenzene (Ia(3))

The title compound (Ia(3)) was synthesized following the method of Example 4 and using the aniline (12) from Example 8. $^1$H NMR (DMSO-d$_6$) δ 5.11 (a, 2, CH2), 6.97 (dd, 1, H4), 7.28 (d, 1, H2), 7.31–7.46 (m, 6, phenyl, H5), 7–96 (d, 1, H6'), 8.33 (d, 1, H5'), 8.34 (s, 1, H3').

Example 11

Synthesis of (4'-Phthalimido)Carboxamido-3-(4-Bromobenzyloxy)-Benzene (Ia(5))

The title compound (Ia(5)) was synthesized following the method of Example 4 and using the aniline:

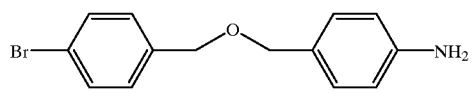

(16)

The aniline (16) was obtained from 3-nitrophenol by first reacting it with 4-bromobenzyl bromide, similar as to the method of Example 8. The intermediate aniline was not independently characterized before using in the synthesis of the title compound (Ia(5)). $^1$H NMR (DMSO-d$_6$) δ5.08 (s, 2, CH$_2$), 6.97–7.09 (2d, 2, H5, H6), 7.13 (d, 2, H2'', H6''), 7.40 (m, 3, H3'', H5'', H4) 7.46 (d, 1, H2), 7.92 (d, 1, H6'), 8.30 (d, 1, H5'), 8.31 (s, 1, H3').

Example 12

Enzyme and Cell Culture Assays

Enzyme Assays: Recombinant *T. foetus* HGXPRT and human HGPRT were isolated from *E. coli* strain SØ606, transformed with pBTfprt and pBAcprt expression plasmids, respectively (Chin, et al., *Mol. Biochem. Parasitol.* 63:221–229 (1994); Kanaaneh, et al., *Eur. J. Biochem.* 223:595–601 (1994)). Spectrophotometric enzyme assays were performed as described in Yuan, et al., *Biochemistry* 31:806–810 (1992). The compounds tested were dissolved in DMSO-d$_6$, and concentrations were determined by integration of NMR peaks with methylene chloride as an internal standard. The concentration of DMSO in the assays was kept at 10%.

The results are presented in Table 1. Preferred compounds include the derivatives of 3-aminophthalimide (compound Id(1)) and 3-benzyloxyaniline (compound Ia(1)), with IC$_{50}$ values of 5 and 16 μM, respectively. In addition, compounds Ia(5) and Ia(6) were also active inhibitors, representing a 10-fold increase in affinity for *T. foetus* HGXPRT compared to compound Ia(1). Compound Ia(12) also faired reasonably well.

Cell Culture Assays: *T. foetus* strain kv1 trophozoites were cultivated in Diamond's TYM medium at 37° C. Cell densities in time samples were determined using a hemocytometer. The concentration of DMSO in culture medium was maintained at or below 1%, which had no apparent effect on cell growth.

All of the compounds assayed were shown to be concentration-dependent inhibitors of *T. foetus* growth in culture. The ED$_{50}$ values are reported in Tables 1. Interestingly, the ED$_{50}$ values for all of the assayed phthalimidocarboxanilides, were within 20% of their respective IC$_{50}$ values, serving as another indirect confirmation of the mode of action of these phthalimide derivatives.

If the designed compounds act within the cells as competitive inhibitors of HGXPRT, addition of the substrate they are competing with would be expected to reverse the growth inhibition (Somoza, et al., *Biochemistry* 37:5344–5348 (1998)). Indeed, compound Ia(5)-induced inhibition of *T.* foetus growth was reversed by increasing the concentration of hypoxanthine in the growth medium. A minimum hypoxanthine concentration between 0.2 and 0.5 mM was required for the survival of the cells challenged with 5 μM of compound Ia(5). Hypoxanthine at concentrations>1 mM essentially abolished any inhibition of cell proliferation under these experimental conditions.

TABLE 1

Inhibition of *T. foetus* HGXPRT ($IC_{50}$) and in vitro growth of *T. foetus* ($ED_{50}$)

| Compound # | $IC_{50}$, μM | $ED_{50}$, μM |
|---|---|---|
| Ic(1) | 53 | ND |
| Ib(1) | 33 | 39 |
| Ia(1) | 16 | 19 |
| Id(1) | 5 | ND |
| Ia(2) | 28 | ND |
| Ia(3) | 8 | ND |
| Ia(4) | 3 | 3.9 |
| Ia(5) | 1.5 | 2.8 |
| Ia(6) | 1.7 | ND |
| Ia(7) | 8.2 | ND |
| Ia(8) | 3.5 | ND |
| Ia(9) | 8.9 | ND |
| Ia(10) | 4.3 | 5.1 |
| Ia(11) | 6.5 | ND |
| Ia(12) | 3.5 | 4.6 |
| Ia(13) | 12.1 | ND |
| Ia(14) | 7.1 | ND |
| Ia(15) | 5.2 | ND |
| Ia(16) | 9.3 | ND |

ND = Not determined

Compounds showing high activity were tested for inhibition of human HGPRT (Table 2). All of the inhibitors were selective for *T. foetus* HGXPRT, but the extent of selectivity varied. Compounds Ia(4) and Ia(10) were approximately 100-fold more selective, Ia(5) was 30-fold more selective, and Ia(12) displayed the lowest selectivity in this series (7X).

TABLE 2

Selective Inhibition of *T. foetus* HGXPRT ($IC_{50}$)

| Compound # | $IC_{50}$, μM *T. foetus* HGXPRT | $IC_{50}$, μM Human HGXPRT |
|---|---|---|
| Ia(4) | 3 | >50(82.4%)* |
| Ia(5) | 1.5 | 45 |
| Ia(10) | 4.3 | >50(88.3%)* |
| Ia(12) | 3.5 | 24 |

According to the model based upon structure-based drug design and combinatorial chemistry, compound Ia(5) was expected to act as a competitive inhibitor of HGXPRT. Indeed, experimental data regarding induced inhibition of *T. foetus* HGXPRT, indicated a competitive mode of inhibition by compound Ia(5) with respect to guanine with a K of 0.49±0.03 μM.

Example 13

This example illustrates the preparation of a representative pharmaceutical formulation for oral administration containing an active compound of Formula I, e.g. (4'-phthalimido) carboxamido-3 -(4-bromobenzyloxy)-benzene.

| Ingredients | Quantity per tablet, mg |
|---|---|
| Active Compound | 200 |
| Lactose, spray-dried | 148 |
| Magnesium stearate | 2 |

The above ingredients are mixed and introduced into a hard-shell gelatin capsule.

Other compounds of Formula I can be used as the active compound in the preparation of the orally administrable formulations of this example.

Example 14

This example illustrates the preparation of another representative pharmaceutical formulation for oral administration containing an active compound of Formula I, e.g., (4'-phthalimido)carboxamido-3-(4-bromobenzyloxy)-benzene.

| Ingredients | Quantity per tablet, mg |
|---|---|
| Active Compound | 400 |
| Cornstarch | 50 |
| Lactose | 145 |
| Magnesium stearate | 5 |

The above ingredients are mixed intimately and pressed into single scored tablets.

Other compounds of Formula I can be used as the active compound in the preparation of the orally administrable formulations of this example.

Example 15

This example illustrates the preparation of a representative pharmaceutical formulation containing an active compound of Formula I, (4'-phthalimido)carboxamido-3-(4-bromobenzyloxy)-benzene. An oral suspension is prepared having the following composition.

| Ingredients | Amount |
|---|---|
| Active Compound | 1.0 g |
| Fumaric acid | 0.5 g |
| Sodium chloride | 2.0 g |
| Methyl paraben | 0.1 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

Other compounds of Formula I can be used as the active compound in the preparation of the orally administrable formulations of this example.

Example 16

This example illustrates the preparation of a representative pharmaceutical formulation for injection containing an active compound of Formula I, e.g. (4'-phthalimido) carboxamido-3-(4-bromobenzyloxy)-benzene. An injectable preparation buffered to a pH of 4 is prepared having the following composition:

| Ingredients | Amount |
| --- | --- |
| Active Compound | 0.2 g |
| Sodium Acetate Buffer Solution (0.4 M) | 2.0 ml |
| HCl (1N) | q.s. to pH 4 |
| Water (distilled, sterile) | q.s. to 20 ml |

Other compounds of Formula I can be used as the active compound in the preparation of the injectable formulations of this example.

Example 17

This example illustrates the preparation of a representative pharmaceutical formulation for topical application containing an active compound of Formula I, e.g., (4'-phthalimido)carboxamido-3-(4-bromobenzyloxy)-benzene.

| Ingredients | grams |
| --- | --- |
| Active compound | 0.2–10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. to 100 g.

Other compounds of Formula I can be used as the active compound in the preparation of the topical formulations of this example.

Example 18

This example illustrates the preparation of a representative pharmaceutical formulation containing an active compound of Formula I, e.g., (4'-phthalimido)carboxamido-3-(4-bromobenzyloxy)-benzene. A suppository totaling 2.5 grams is prepared having the following composition:

| Ingredients | Amount |
| --- | --- |
| Active Compound | 500 mg |
| Witepsol H-15* | balance |

(*triglycerides of saturated vegetable fatty acid; a product of Riches-Nelson, Inc., New York, N.Y.)

Other compounds of Formula I can be used as the active compound in the preparation of the suppository formulations of this example.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of the formula:

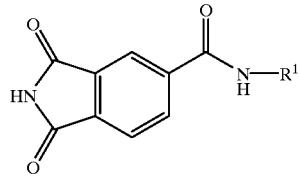

wherein:

$R^1$ is selected from the group consisting of:

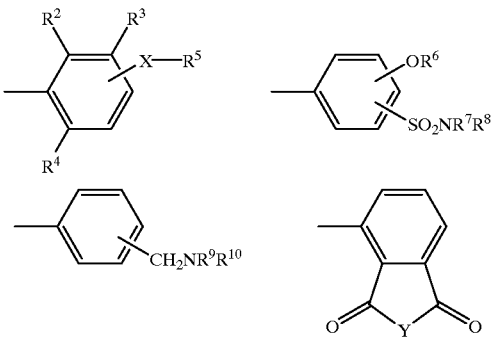

and a fused three-membered aryl or heteroaryl group; $R^2$, $R^3$ and $R^4$ are independently selected from the group consisting of H, lower alkyl and halo; X is selected from the group consisting of —$CH_2$—O— and —O—$CH_2$—; $R^5$ is aryl; $R^6$, $R^7$ and $R^8$ are independently selected from the group consisting of H and lower alkyl; $R^9$ is lower alkyl and $R^{10}$ is a cyclic aliphatic ring, or $R^9$ and $R^{10}$ can be taken together to form a cyclic aliphatic ring; and Y is selected from the group consisting of NH and O; or the pharmaceutically acceptable salts thereof.

2. The compound of claim 1 where $R^1$ is:

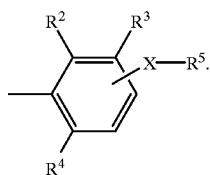

3. The compound of claim 2 where $R^2$ is selected from the group consisting of H and halo.

4. The compound of claim 2 where $R^3$ is selected from the group consisting of H and lower alkyl.

5. The compound of claim 2 where $R^4$ is selected from the group consisting of H, lower alkyl and halo.

6. The compound of claim 2 where $R^5$ is selected from the group consisting of phenyl, substituted phenyl and naphthyl.

7. The compound of claim 1 where $R^1$ is:

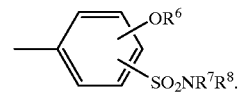

8. The compound of claim 7 where $R^6$ is lower alkyl.

9. The compound of claim 7 where $R^7$ is lower alkyl.

10. The compound of claim 7 where $R^8$ is lower alkyl.

11. The compound of claim 1 where $R^1$ is:

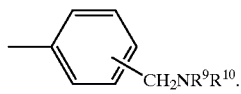

12. The compound of claim 11 where $R^9$ is lower alkyl and $R^{10}$ is a cyclic aliphatic ring.

13. The compound of claim 1 where $R^1$ is:

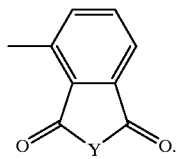

14. The compound of claim 13 where Y is NH.

15. The compound of claim 13 where Y is O.

16. The compound of claim 1 where $R^1$ is a fused three-membered aryl or heteroaryl group.

17. The compound of claim 16 where $R^1$ is anthryl or acridinyl.

18. A pharmaceutical composition for the treatment of parasitic protozoa infections in mammals by inhibiting hypoxanthine-guanine-xanthine phosphoribosyltransferase or guanine phosphoribosyltransferase in the purine salvage pathways of said parasitic protozoa, which composition comprises the compound of claim 1 in a pharmaceutically acceptable carrier.

19. A method of treating in mammals a parasitic protozoa infection that is alleviated by treatment with an inhibitor of hypoxanthine-guanine-xanthine phosphoribosyltransferase or guanine phosphoribosyltransferase in the purine salvage pathways of parasitic protozoa, which method comprises administering to a mammal in need of such treatment a therapeutically effective amount of the compound of claim 1.

20. The method of claim 19 wherein the disease state is bovine trichomomasis.

21. The method of claim 19 wherein the disease state is giardiasis.

22. The method of claim 19 wherein said compound is in a pharmaceutical composition which contains a pharmaceutically acceptable carrier.

* * * * *